US006436388B2

(12) United States Patent
Kudo et al.

(10) Patent No.: US 6,436,388 B2
(45) Date of Patent: Aug. 20, 2002

(54) METHOD OF TREATING RHABDOMYOLYSIS BY ADMINISTERING HEPATOCYTE GROWTH FACTOR

(76) Inventors: Ikue Kudo; Tomokazu Nagano, both of c/o Sumitomo Pharmaceuticals Co., Ltd., 1-98, Kasugade Naka 3-chome, Konohana-ku, Osaka-shi, Osaka 554-0022 (JP)

( * ) Notice: Subject to any disclaimer, the term of this patent is extended or adjusted under 35 U.S.C. 154(b) by 0 days.

(21) Appl. No.: 09/381,031

(22) PCT Filed: Mar. 12, 1998

(86) PCT No.: PCT/JP98/01081

§ 371 (c)(1),
(2), (4) Date: Feb. 24, 2000

(87) PCT Pub. No.: WO98/41227

PCT Pub. Date: Sep. 24, 1998

(30) Foreign Application Priority Data

Mar. 15, 1997 (JP) ................................. 9-82235

(51) Int. Cl.$^7$ .......................... A61K 45/00; A61K 38/00
(52) U.S. Cl. ...................... 424/85.1; 424/198.1; 514/2; 514/12
(58) Field of Search ................ 424/184.1, 198.1, 424/85.1; 435/325, 810, 4; 514/2, 12, 21; 530/350, 399

(56) References Cited

U.S. PATENT DOCUMENTS 5,091,180 A * 2/1992 Walker et al. ............... 424/944
5,360,790 A * 11/1994 Humes ......................... 514/12
5,703,048 A * 12/1997 Roos et al. .................... 514/12

FOREIGN PATENT DOCUMENTS

| EP | 0462549 A | 12/1991 |
| JP | 3255096 | 11/1991 |
| JP | 5111383 | 5/1993 |
| WO | WO 97/12629 | * 4/1997 |

OTHER PUBLICATIONS

Reinhold et al. Lancet 349: 540–541, 1997.*
Zurovsky, Y. J Basic Clin Physiol Pharmacol 3: 223–237, 1992.*
Lake, EW et al. Seminars in Nephrology 14(1): 83–97, 1994.*
Wang, S. et al. Nephrology Dialysis Transplantation 12(8): 1560–1563, 1997.*
Toback, FG. Kidney International 41: 226–246, 1992.*
Mendley, SR et al. Annual Review of Physiology 51: 33–50, 1989.*
Matsumoto, K. et al. Ciba Foundation Symposium 212: 198–214, 1997.*
Harper, J. Critical Care Nurse 10(3): 32–36, 1990.*
Igawa et al., Am.J. Physiol., vol. 265, No. 1 PT 2, 1993 pp. F61–F69, XP002069360.
Kawaida et al., Proc. Natl. Acad. Sci., vol. 91, No. 10, 1994, pp. 4357–4361, XP002069361.
Goto et al., vol. 77, No. 4, 1997, pp. 440–444 XP002069362.
Woodrow et al., Renal Failure, vol. 17, No. 4, 1995, pp. 467–474, XP002069363.
Tomiya, Tomoaki et al., Nephron 1996, 73:735.
Nakamura, Toshikazu et al., Nature vol. 342, 1989, 440–443.
Miller, Steven B. et al., American Physiological Society, 1994, 266, 129–134.
Common Diease Series 17: Zinfuzen 57–61, Nankodo, 1991 and Abstract therewith.
Jin to Touseki (Kidney & Dialysis) vol. 31, 1991, 395–399 and Abstract therewith.

* cited by examiner

Primary Examiner—Gary L. Kunz
Assistant Examiner—Bridget E. Bunner
(74) Attorney, Agent, or Firm—Birch, Stewart, Kolasch & Birch, LLP.

(57) ABSTRACT

The present invention is drawn to a method of treating acute renal failure caused by rhabdomyolysis by administering a therapeutically effective amount of hepatocyte growth factor (HGF). The present invention is further drawn to a method of treating rhabdomyolysis by administering a therapeutically effective amount of hepatocyte growth factor (HGF).

2 Claims, 2 Drawing Sheets

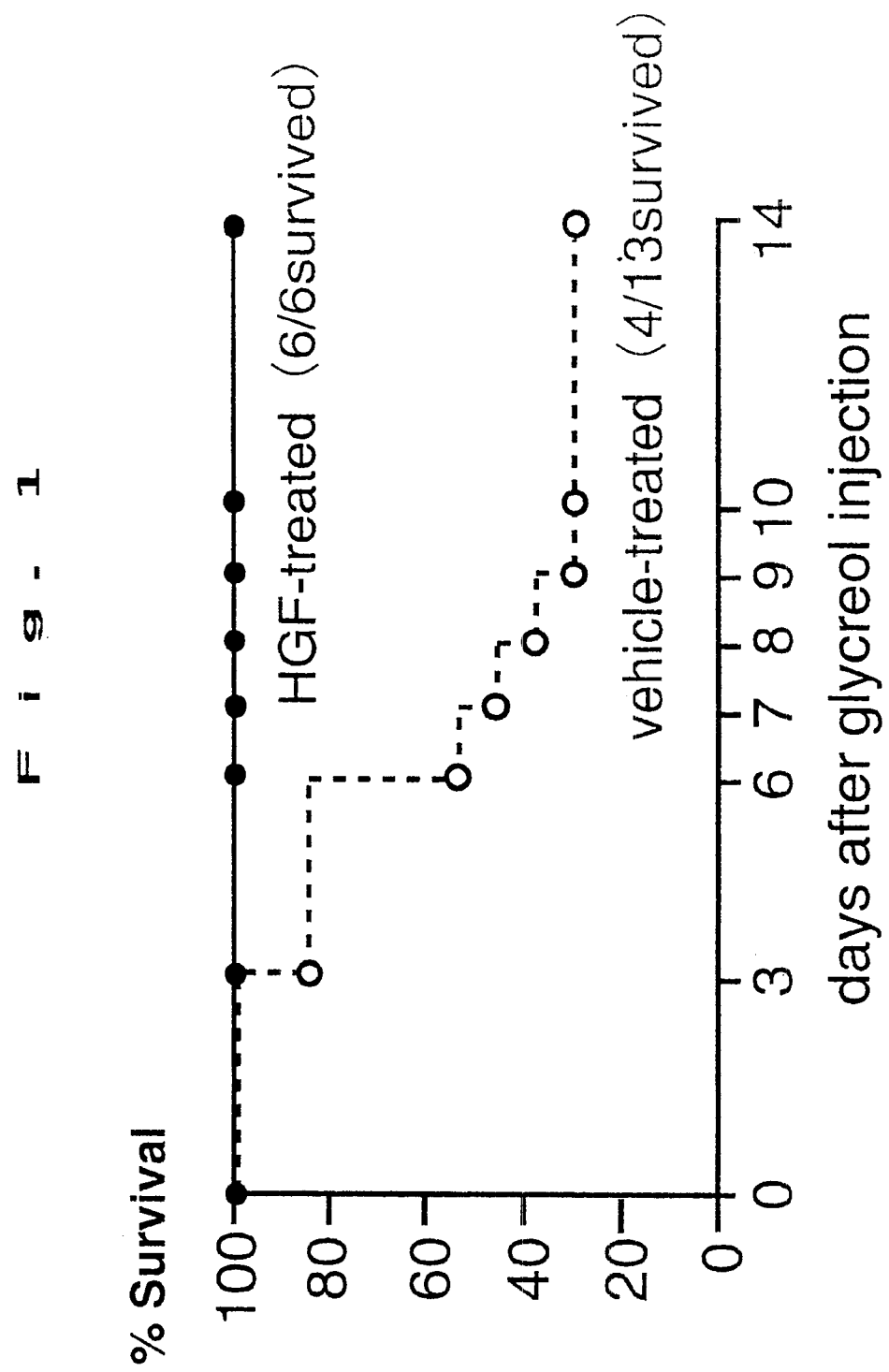

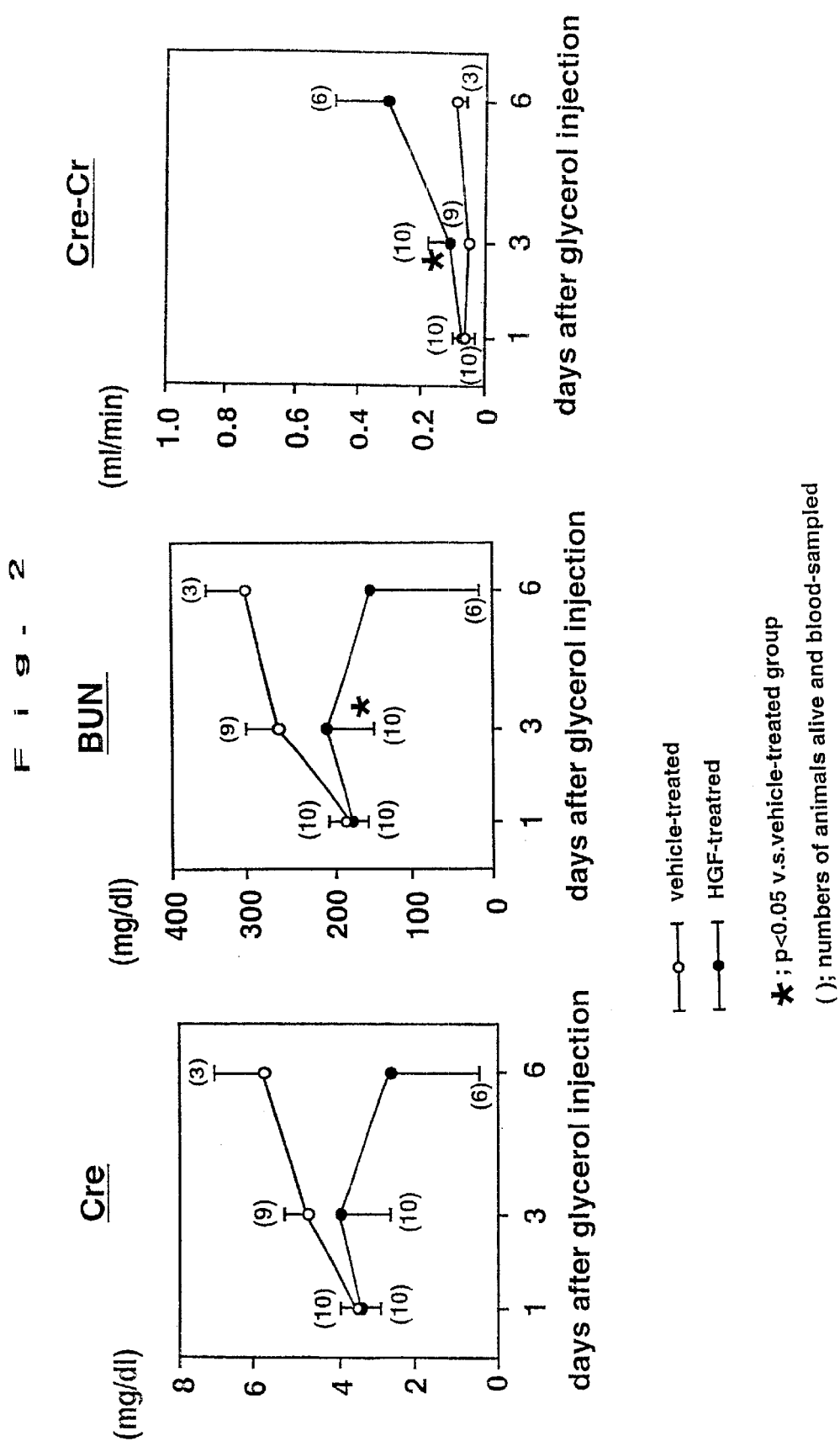

METHOD OF TREATING RHABDOMYOLYSIS BY ADMINISTERING HEPATOCYTE GROWTH FACTOR

This application is the national phase under 35 U.S.C. §371 of PCT International Application No. PCT/JP98/01081 which has an International filing date of Mar. 12, 1998, which designated the United States of America.

BACKGROUND OF THE INVENTION

Acute renal failure is defined as having symptoms of azotemia, electrolyte imbalance, uremia and the like caused by acute renal dysfunction. Acute renal failure is classified into prerenal acute renal failure, renal acute renal failure and postrenal acute renal failure caused by renal dysfunction. Renal acute renal failure is classified into (1) vasculitis, glomerular lesion, (2) acute interstitial nephritis, (3) tubule obstruction and (4) acute renal failure in a narrow sense. Acute renal failure in a narrow sense is caused by acute tubular necrosis. The acute renal failure in a narrow sense results from (1) ischemia, (2) nephrotoxic substance, or (3) myolytic substance (e.g. myoglobin) and so on.

Ischemic acute renal failure is caused by bleeding from surgery, shock, external injury, burn and the like. Experimental animal model for ischemic acute renal failure is exemplified by renal artery ligation. In the rat model, BUN (blood urea nitrogen) and serum creatinine are increased, HGF (Hepatocyte Growth Factor) mRNA expression is enhanced 6 to 12 hours after ischemia, and then HGF bioactivity in rat kidney and plasma is activated (American Journal of Physiology, 1993; 265; 61–69).

Acute renal failure is also caused by a nephrotoxic substance such as anti-biotic agent, antitumor agent, contrast medium. An experimental animal model of acute renal failure caused by a nephrotoxic substance is made by administration of a compound such as mercurous chloride, cisplatin, and contrast medium to rats. Mercurous chloride administered rats show an increase of BUN and creatinine, enhancement of HGF mRNA expression and activity of HGF (Nephron 1996; 73: 735), as reported on ischemia model. It is suggested that HGF be involved in restoring a patient from renal failure.

It is reported that renal dysfunction in experimental animal models caused by ischemia or a nephrotoxic substance such as mercurous chloride and cisplatin is recoverable by HGF administration (American Journal of Physiology, 1994; 266; 129–134, Proc. Natl. Acad. Sci. 1994; 91; 4537–4361). In both models, the increase of BUN and creatinine is recovered rapidly by HGF administration. It is considered that HGF acts as a renotropic factor to enhance proliferation of damaged tubular cells.

Myolytic substances (such as myoglobin, phosphate, potassium, and uric acid) are released by external injury, compression damage (e.g. crash syndrome), burn, infection, drug poisoning (e.g. alcohol, barbitur derivatives), muscle metabolic disease, overuse of muscle, hypophosphatemia, snake venom and the like and show toxicity to tubular cells. As a result, necrosis of tubular cells occurs, and necrotic cells and protein (hyaline) casts bring tubular obstruction. It is also reported that myoglobin reduces renal blood flow. The above mentioned mechanism is considered to cause acute renal failure caused by rhabdomyolysis (Common Disease Series 17: Zinfuzen (renal failure), 57–61, Nankoudo, (1991)).

Clinical symptoms of rhabdomyolysis are: (1) increase in muscle derived enzyme such as creatine phosphate kinase, lactate dehydrogenase, aldolase, glutamic-oxaloacetic transaminase: (2) enhanced uptake of $^{99m}$TC-pyrophosphate into injured muscle; (3) presence of myoglobin; (4) BUN/ serum creatinine ratio of 10–20 or under; (5) hyperuricemia; and (6) hyperphosphatemia, hypocalcemia and hyperpotassemia.

The methods of treatment for rhabdomyolisis include fluid replacement therapy, administering diuretics, fascia release therapy, plasmapheresis, antiplatelet therapy, but these methods of treatment are not adequate for a severe or poor prognosis. There is no adequate method of treating or preventing acute renal failure caused by rhabdomyolysis or pharmaceutical composition for treating or preventing acute renal failure caused by rhabdomyolysis.

There is also no adequate method of treating or preventing hemolytic uremic syndrome (HUS) or a pharmaceutical composition for treating or preventing HUS. Clinical characterization of HUS is thrombocytopenia, microangiopathic hemolytic anemia, and symptoms of acute renal failure. The cause of HUS are infection (e.g. O157), hereditary, administration of drug (e.g. cyclosporin), pregnancy, organ graft, SLE, hypertension, different group blood transfusion and the like. Hemolysis is caused by the above conditions, and then hemoglobin and the like are released, and HUS occurs as a result.

A glycerol-induced animal model is well known for use in modeling acute renal failure. When glycerol is injected into the muscle of animals, hyperosmolarity of glycerol causes hemolysis in muscle cells and intramuscular vessel in the animal model. Myoglobin, hemoglobin, potassium and other rhabdomyolytic substances are released into the blood and damage renal cells. Dehydration in the animal model further enhances the toxicity of the rhabdomyolytic substances. As a result severe decrease of renal blood flow and ischemia are caused, and severe glomerular filtration causes oliguresia and anuria. The part of muscle where glycerol is administered becomes a place to store bodily fluid, and systemic circulation, blood flow rate, and cardiac output are reduced (JINSIKKAN MODEL (a model for renal disease), JIN TO TOUSEKI (kidney and dialysis) Vol. 31 (1991) 395–399). If the model animal is deprived of water before the administration of glycerol, the effect of myolytic substances is enhanced and rhabdomyolytic model is induced.

BRIEF DESCRIPTION OF THE INVENTION

The present invention provides a pharmaceutical composition for treating acute renal failure caused by rhabdomyolysis comprising a therapeutically effective amount of HGF.

The present invention provides a method of treating acute renal failure caused by rhabdomyolysis comprising administering a therapeutically effective amount of HGF to a patient, particularly a human patient, in need thereof.

The present invention further provides a pharmaceutical composition for treating myoglobinuria comprising a therapeutically effective amount of HGF.

The present invention further provides a method of treating acute renal failure caused by rhabdomyolysis caused by a myolytic substance released by external injury, compression damage (e.g. crash syndrome), burn, infection, drug poisoning (e.g. alcohol, barbitur derivative), muscle metabolic disease, overuse of muscle, hypophosphatemia, snake venom and the like comprising administering a therapeutically effective amount of HGF to a patient in need thereof.

The present invention further provides a pharmaceutical composition for treating acute renal failure caused by rhabdomyolysis caused by a myolytic substance released by external injury, compression damage (e.g. crash syndrome), burn, infection, drug poisoning (e.g. alcohol, barbitur derivative), muscle metabolic disease, overuse of muscle, hypophosphatemia, snake venom and the like comprising a therapeutically effective amount of HGF.

The present invention further provides a pharmaceutical composition for treating hemolytic uremic syndrome comprising a therapeutically effective amount of HGF and a pharmaceutically acceptable carrier.

The present invention further provides a method of treating hemolytic uremic syndrome comprising administering a therapeutically effective amount of HGF to a patient in need thereof.

The present invention further provides a pharmaceutical composition for treating hemolytic uremic syndrome caused by infection (O157), heredity, administration of drug (cyclosporin), pregnancy, organ graft, SLE, hypertension, different group blood transfusion and the like comprising a therapeutically effective amount of HGF and a pharmaceutically acceptable carrier.

The present invention further provides a method of treating hemolytic uremic syndrome caused by infection (e.g. O157), heredity, administration of drug (e.g. cyclosporin), pregnancy, organ graft, SLE, hypertension, different group blood transfusion and the like comprising administering a therapeutically effective amount of HGF to a patient in need thereof.

BRIEF DESCRIPTION OF THE DRAWINGS

FIG. 1 is a graph showing the survival rate of the control group and HGF administered group.

FIG. 2 is a graph showing the biochemical values of serum, urine, and renal function one, three and six days after the administration of glycerol.

DETAILED DESCRIPTION OF THE INVENTION

Hepatocyte growth factor (HGF), which can be used in the present invention, has been already sold or is obtained by the methods described below.

The methods of preparing HGF are well known to a person of ordinary skill in the art. For example, HGF may be prepared by a process comprising the steps of extracting from an organ such as a liver, spleen, lung, bone marrow, brain, kidney, placenta, blood cells such as platelets, white blood cells, plasma, serum and the like of a mammal such as a rat, bovine, horse, sheep and the like, and purifying the extract (FEBS Letters, 224, 312, 1987, Proc. Natl. Acad. Sci. USA, 86, 5844, 1989).

HGF may also be prepared by a process which comprises the steps of culturing primary cells or a cell line which produce(s) HGF, obtaining extract from the cultured product (supernatant fluid, cultured cells, etc), and purifying HGF from the extract.

HGF may be prepared by genetic engineering method comprising the steps of inserting a gene encoding HGF into an appropriate vector, transfecting a host cell with the vector containing the HGF gene, and purifying HGF from the supernatant of the cultured transfected cells (for example Nature, 342, 440, 1989; Japanese patent application KOKAI 5-111383; Japanese patent application KOKAI 3-255096; Biochem. Biophys. Res. Commun., 163, 967, 1989).

The host cell is not limited, and various host cells conventionally used in genetic engineering methods can be used, which are, for example, *Escherichia coli, Bacillus subtilis,* yeast, mold, fungi, plant and animal cells and the like.

A more specific process of preparing HGF from a living tissue comprises the steps of administering carbon tetrachloride to a rat intraperitoneally to induce rat hepatitis, removing a liver from said rat and homogenizing, and purifying the HGF by a conventional method of protein purification such as gel column chromatography (such as S-Sepharose, heparinsepharose and the like), HPLC and the like.

HGF may be prepared by a genetic engineering process comprising the steps of transforming an animal cell (such as Chinese Hamster Ovary (CHO) cells, mouse C127 cells, monkey COS cells, Sf (Spodoptera frugiperda) cells and the like) with a gene encoding an amino acid sequence of HGF, and purifying HGF from the supernatant fluid of said cells.

HGF includes human HGF and mammalian HGF, preferable HGF is a human HGF, and more preferable HGF is a human recombinant HGF (Japanese patent application KOKAI H5-111383 (1993)).

HGF prepared by the above processes includes any HGF that has substantially the same as the full-length HGF, such as a partial deletion derivative of HGF, an amino acid substitution derivative of HGF, an amino acid sequence insertion derivative of HGF, a derivative of HGF caused by binding one or more amino acids to N- terminus or C-terminus of the HGF amino acid sequence, or a sugar chain deleted or substituted HGF.

HGF may be formulated in various ways such as in liquid preparations, solid preparations, capsule preparations, depot preparations and the like. HGF may be formulated for parenteral administration for injection without any carrier or with an appropriate conventional carrier and for oral administration with an appropriate conventional carrier. The formulation for parenteral administration for injection may be prepared by conventional methods known to a person of ordinary skill in the art, such as a method comprising the steps of dissolving HGF in an appropriate solvent such as sterilized water, buffered solution, isotonic sodium chloride solution and the like, sterilizing by filtration and filling said solution in a sterilized bottle. An amount of HGF in the parenteral formulation is from about 0.0002 to about 0.2 (W/W %), and preferred amount is from about 0.001 to about 0.1 (W/W %). The formulation may be prepared by a conventional formulation technique. An amount of HGF may be varied depending on the formulation, the disease to be treated, the symptoms of patient and the like.

HGF may be formulated in rectal compositions such as suppositories or retention enemas, e.g. containing conventional suppository bases such as cocoa butter, water soluble bases (glycerinated gelatin, macrogols, etc.) or other glycerides.

HGF may be administered in a form for inhalation. For administration by inhalation HGF in conveniently delivered in the form of an aerosol spray presentation from pressurized packs or nebulizers, with the use of suitable propellants such as carbon dioxide or other suitable gasses.

HGF may be administered using a conventional drug delivery system well known to a person skilled in the art. Examples of the preparations for a drug delivery system are microspheres (nanoparticle, microparticle, microcupsule, bead, liposome, multiple emulsion, etc.) and the like.

Preferably, a stabilizer may be added to the formulation. Examples of a stabilizer include albumin, globulin, gelatin, mannitol, glucose, dextran, ethylene glycol and the like. The formulation of the present invention may include a necessary additive such as an excipient, a solubilizer, an antioxidizing agent, a pain-alleviating agent, an isotonic agent and the like. The liquid formulation may be stored in a frozen condition, or after removal of water by a process such as freeze-drying. The freeze-dried preparations are dissolved in pure water for injection and the like before use.

Effective dosages and schedules for administering HGF may be determined empirically, and the determination is within the skill of a person of ordinary skill in the art. The administration route of the preparation may vary depending on the form of the preparation. For example, the parenteral preparation may be administered intravenously, intraarterially, subcutaneously or intramuscularly. The amount of administration may vary depending on the symptom, age, weight, etc. of the patient. A dose can be selected from the range of from 0.1 μg to 10 mg/kg of body weight. The preferred range is from 1 μg to 400 μg/kg. The preparation of HGF may be administered once or several (2 or 3) times per day.

HGF may also be formulated as depot preparations. Such long acting formulations may be administered by implantation (for example subcutaneously or intramuscularly) or intramuscular injection. Thus, for example, HGF may be formulated with suitable polymeric or hydrophobic materials (for example as an emulsion in an acceptable oil), ion exchange resins, or as sparingly soluble derivatives, for example as a sparingly soluble salt.

Effective dosages and schedule for administering the depot preparation may be determined empirically, and the determination is within the skill of a person of ordinary skill in the art. The administration route of the depot preparation may vary depending on the form of the preparation.

The preferred mode of administration of the depot preparations is once for at least one week, preferably once for at least one month.

It is an object of this invention to provide a packaged product, kit or article of manufacture for treating acute renal failure caused by rhabdomyolysis or myoglobinuria, which contains HGF. The packaged product may comprise a container which contains a therapeutically effective amount of HGF for treating acute renal disease caused by rhabdomyolysis or myoglobinuria, and instructions associated with the container which indicates that HGF can be used for treating acute renal disease caused by rhabdomyolysis or myoglobinuria. For example, the HGF can be placed into a sterile vial, which can then be placed into another container such as a box. Instructions for administering the drug in accordance with the present invention can be placed on a label on the vial and/or on the box and/or can be inserted in the box as a package insert.

EXAMPLES

The following examples are for illustrative purposes only and are not to be construed as limiting the invention.

Example 1

Materials
Animals

Male wistar rats(seven weeks old) were purchased from NIHON SLC (Shizuoka, Japan), and were raised preliminarily for three days. Male wistar rats (7.5 weeks old, weight: about 200 g) were used in the following examples.
Method of Acute Renal Failure Model A 50% glycerol solution in saline was prepared and was intramuscularly administered to rats (10 ml/kg) that were deprived from water for 15 hours before the administration under anesthesia caused by diethylether. 8 hours after the administration the rat were able to drink water freely.
Agent Administered Recombinant human hepatocyte growth factor (hHGF) was diluted to 125 μg/ml with an HGF solution. A dosage was 2 ml/kg (250 μg/ml) was administered via caudate vein.

HGF solution was 10 mM sodium citrate aqueous solution which includes 0.3 M NaCl and 0.01% Tween 80.
Administration Rats were divided into two groups, one was the control group and the other was hHGF administered group. hHGF solution was administered to one group 1 hour before the glycerol administration and hHGF solution was also administered to the group 1, 3, 5, 8, 24, and 36 hours after the glycerol administration. 1 ml of saline was administered to the control group 1 and 3 hours after the glycerol administration. 1 ml of water was also administered to the control group 5 and 8 hours after the glycerol administration.
Observation of Symptoms The survival rate of the rats was observed for 14 days after the administration of the glycerol.
Results Rats were induced with severe acute renal failure by the glycerol administration and the value of serum BUN and serum creatinine two days after much were increased (the value of serum creatinine: control group=5.1±1.2 mg/dl, HGF administration group=4.2±0.8 mg/dl).

FIG. 1 shows the survival rate of rats. In the control group death of rats was observed from 3 days after the glycerol administration, and 9 of 13 rats were dead within 9 days. Immediately after the death, the rat underwent postmortal examination, and the appearance of renal was observed to be quite different. Necrosis of the uriniferous tubule in renal cortex was observed. In the HGF administration group death was not observed during the experiment. The survival rate of 14 days after the glycerol administration was analyzed by x-square test, and the survival rate of the HGF administration group was significantly higher(P<0.01) than the control group.

Example 2

Material
Experimental Animals

Male wistar rats (seven weeks old) were purchased from NIHON SLC (Shizuoka, Japan), and were raised preliminarily for three days. Male wistar rats (7.5 weeks old, weight: about 200 g) were used in the following examples.
Method of Acute Renal Failure Model A 50% glycerol solution in saline was prepared and was intramuscularly administered to the rats(10 ml/kg) that were deprived from water for 15 hours before the administration under anesthesia by diethylether. 8 hours after the administration the rats were able to drink water freely.
Agent Administered Recombinant human hepatocyte growth factor (hHGF) was diluted to 125 μg/ml with saline. A dosage was 2 ml/kg (250 μg/ml) was administered via caudate vein.
Administration Rats were divided into two groups, one was the control group (n=10) and the other was hHGF administered group (n=10). hHGF solution was administered to one group 1 hour before the glycerol administration and 1, 3, 5, 8, 24, and 36 hours after the glycerol administration. 1 ml of saline was administered to the control group 1 and 3 hours after the glycerol administration and 1 ml of water was administered to the control group 5 and 8 hours after the glycerol administration.

Measurement of Biochemical Value of Serum and Urine

Serum was obtained from arteria caudalis under anesthesia by diethylether 1, 3 and 6 days after the glycerol administration. The amount of serum urea nitrogen (BUN) and serum creatinine (Cre) were measured by ultramicro multipurpose biochemical automatic analyzer, CHEM1. 12-hour urine was collected 1, 3 and 6 days after the glycerol administration using a metabolic cage. The amount of the urine was measured. The amount of creatinine in the urine was measured by ultramicro multipurpose biochemical automatic analyzer, CHEM1. From the analysis of the data above clearance of endogenous creatinine was derived from the equation described below.

$$\text{Clearance of endogenous creatinine} = \frac{\text{Urine creatinine value (mg/dl)} \times \text{12-hour urine collection (ml)}}{\text{Serum creatinine value (mg/dl)} \times \text{urine collection time (720 min)}}$$

Observation of Symptoms

The survival of the rats was observed for fifteen days after the administration of glycerol.

Statistical Processing

The survival rate of 15 days after glycerol administration was analyzed by X-square test.

Serum biochemical values obtained 1 and 3 days after the glycerol administration was analyzed by t-test or Welch-test.

Results

Survival Rate

In the control group, the survival rate of rats was observed from 3 days after the glycerol administration, and 7 of 10 rats died within 9 days. In the HGF administration group, 2 of 10 rats died during the experiment. The survival rate of the HGF administration group was significantly higher ($p<0.05$) than the control group.

The Biochemical Value of Serum and Urine and Function of Kidney

FIG. 2 shows the biochemical value obtained from serum, urine and function of the kidney.

In the control group, beginning one day after the glycerol administration, significant increase in values of serum BUN and creatinine was observed, and the values got worse for 6 days. Endogenous clearance of creatinine was kept at 0.1 or below and symptoms of severe renal failure were observed.

On the contrary, in the HGF administered group, a decrease of serum BUN was observed for three days after the glycerol administration, which was accompanied by significant suppression ($p<0.05$) of acute renal failure. At the same time endogenous clearance of creatinine was also significantly improved ($p<0.05$).

Example 3

Materials

Animals

Male wistar rats(seven weeks old) were purchased from NIHON SLC (Shizuoka, Japan), and were raised preliminarily for three days. Male wistar rats (7.5 weeks old, weight: about 200 g) were used in the following examples.

Acute Renal Failure Model

A 50% glycerol solution in saline was prepared and was intramuscularly administered to the rats (10 ml/kg) that were deprived from water for 15 hours before the glycerol administration under anesthesia by diethylether. The rats were able to drink water freely after 8 hours from the glycerol administration.

Agent Administered

Recombinant human hepatocyte growth factor (hHGF) was diluted to 125 µg/ml with an HGF solution. A dosage of 2 ml/kg (250 µg/ml) was administered via caudate vein.

Administration

Rats were divided into two groups, one was the control group (n=8) and the other was hHGF administered group (n=8). hHGF solution was administered to one group 1 hour before the glycerol administration and 1, 3, 5, 8, 24, and 36 hours after the glycerol administration. 1 ml of saline was administered to the control group 1 and 3 hours after the glycerol administration and 1 ml of water was administered to the control group 5 and 8 hours after the glycerol administration.

Analysis of Renal Tissue

Rats were killed 3 days after the glycerol administration, and the kidney was extracted, fixed by formalin phosphate buffer and embedded in paraffin. Renal microtome was made from paraffin-embedded tissue and was PAS stained. A light manifest image of renal cortex of microtome of each rat was taken, and the degree of renal cortex tubular cell necrosis was analyzed. Analysis was made by scoring as weak, moderate and severe. The difference between the control group and HGF administered group was determined by x-test.

Result

Tissue Damage of Renal Tubular Cells

The scores of renal tissue damage are shown in Table 1. In the HGF administered group, damage was suppressed significantly in contrast to the control group.

TABLE 1

|  | Severe | Moderate | Weak |
| --- | --- | --- | --- |
| Control group | 6 | 1 | 1 |
| HGF administrated group | 0 | 4 | 4 |

What is claimed is:

1. A method of treating rhabdomyolysis comprising administering a therapeutically effective amount of hepatocyte growth factor (HGF) to a patient suffering from rhabdomyolysis.

2. A method of treating rhabdomyolysis caused by a myolytic substance released by external injury, compression damage, crash syndrome, burn, infection, drug poisoning, muscle metabolic disease, over use of muscle, hypophosphatemia, or snake venom comprising administering a therapeutically effective amount of hepatocyte growth factor (HGF) to a patient suffering from rhabdomyolysis caused by a myolytic substance released by external injury, compression damage, crash syndrome, burn, infection, drug poisoning, muscle metabolic disease, over use of muscle, hypophosphatemia, or snake venom.

* * * * *